United States Patent [19]

Berridge

[11] Patent Number: 5,082,980
[45] Date of Patent: Jan. 21, 1992

[54] PROCESS AND APPARATUS FOR SYNTHESIZING OXYGEN-15 LABELLED BUTANOL FOR POSITRON EMISSION TOMOGRAPHY

[75] Inventor: Marc S. Berridge, Solon, Ohio

[73] Assignee: Case Western Reserve University, Cleveland, Ohio

[21] Appl. No.: 537,312

[22] Filed: Jun. 13, 1990

[51] Int. Cl.$^5$ ............... C07C 29/09; C07C 29/76; C07C 31/12

[52] U.S. Cl. ................... 568/917; 422/212; 568/887

[58] Field of Search .................. 568/917, 887

[56] References Cited

U.S. PATENT DOCUMENTS

| | | | |
|---|---|---|---|
| 2,925,437 | 2/1960 | Brown | 568/887 |
| 3,078,308 | 2/1963 | Brown | 568/887 |
| 3,194,934 | 7/1965 | Presswood | 568/887 |
| 3,485,879 | 12/1969 | Mameniskis et al. | 568/917 |
| 4,343,623 | 8/1982 | Kulprathipanj et al. | 568/917 |
| 4,543,432 | 9/1985 | Shih et al. | 568/917 |

Primary Examiner—J. E. Evans
Attorney, Agent, or Firm—Fay, Sharpe, Beall, Fagan, Minnich & McKee

[57] ABSTRACT

The present invention is directed to a process and apparatus for synthetically producing $^{15}$O-labeled butanol for position emission tomography. A procedure and apparatus have been developed for the routine rapid and sequential synthesis of oxygen-15 labeled butanol in the amounts and with the purity suitable for use in clinical position tomography. This procedure can replace oxygen-15 labeled water which is more commonly used for routine application, as well as the prior art processes for producing oxygen-15 labeled butanol.

18 Claims, 5 Drawing Sheets

PROCESS AND APPARATUS FOR SYNTHESIZING OXYGEN-15 LABELLED BUTANOL FOR POSITRON EMISSION TOMOGRAPHY

BACKGROUND OF THE INVENTION

The present invention is directed to an improved process and apparatus for producing oxygen-15 ($^{15}$O)-labeled butanol with sufficient product yield and purity for position emission tomography. In addition, the present invention is directed to the purified $^{15}$O-labeled butanol produced by the process of the invention, as well as to the use of the purified $^{15}$O-labeled butanol for the clinical diagnosis.

Positron emission tomography (PET) is a procedure that produces transverse sectional images of the body by the demonstration of the internal distribution of positron-emitting radionuclides. Along these lines, positron emission tomography uses measurements of the back-to-back emission of gamma rays from the annihilation of positrons emitted by radioactive tracers to map the distribution of these tracers in the human body.

One important function of positron emission tomography is the non-invasive assessment of regional cerebral blood flow (CBF) through the use of a number of well-known methods which rely on mathematic modeling of the distribution and/or kinetics of a particular highly retained or freely diffusible tracer (Berridge, M. S., Franceschini, M. P., Tewson, T. J., and Gould, K. L., Preparation of oxygen-15 butanol for positron tomography, *J. Nucl. Med.* 27, pp. 834-839, 1986). In this regard, a number of tracers have been developed for positron emission tomography. For example, oxygen-15($^{15}$O)-labeled water is fairly commonly used for cerebral blood flow measurements. However, while $^{15}$O labeled water has proved to be useful, it reportedly leads to an underestimation of cerebral blood flow in areas of high flow rate because of a limitation of water extraction in the brain tissue (Murakami, M., Hagami, E., Sasaki, H., et al., Radiosynthesis of $^{15}$O labeled butanol for clinical use, *6th Int. Sym. Radiopharm. Chem.*, 81, 1986).

Furthermore, because butanol exhibits a greater degree of lipid solubility which results in the near complete free exchange of butanol into brain tissue, butanol, as opposed to water, has been recommended as being more ideally suited for use in measuring cerebral blood flow (Raichle, M. E., Martin, W. R. W., Herscovitch, P., Kilbourn, M. R., and Welch, M. J., *J. Nucl. Med.*, 24, P63, 1983). Along this line, labeled butanol has now been shown to be a more accurate region cerebral blood flow tracer than labeled water and lower alcohols by studies of animal and human subjects. These studies, performed with radiocarbon labels such as $^{11}$C (Hack, S. N., Bergmann, S. R., Eichling, J. O., et al., Quantification of region myocardial perfusion by exponential infusion of [C-11]-butanol, *IEEE Trans. Biomed. Eng.*, 30, pp. 716-722, 1983; Knapp, W. H., Helus, F., Oberdorfer, et al., $^{11}$C-Butanol for imaging of the blood flow distribution in tumor bearing animals, *Eur. J. Nucl. Med.*, 10, pp. 540-548, 1985; Van Uitert, R. L., Sage, J. I., Levy, D. E., and Duffy, T. E., Comparison of radiolabeled butanol and iodantipyrine as cerebral blood flow markers, *Brain Research*, 222, pp. 365-372, 1981; Herscovitch, P., Raichle, M. E., Kilbourn, M. R., Welch, M. J., Positron emission tomography measurement of cerebral blood flow and permeability - surface area product of water using [$^{15}$O] water and [$^{11}$O] butanol, *J. Cerebral Blood Flow and Metabolism*, 7, pp. 527-542, 1987; Raichle, M. E., Eichling, J. O., Straatman, M. G., Welch, M. J., Larson, K. B., and Ter-Pogossian, M. M., Blood-brain barrier permeability of $^{11}$C labeled alcohols and 15O labeled water, *Am. J. of Physiology*, 230, pp. 543-552, 1976; Kothari, P. J., Finn, R. D., Vora, M. M., Boothe, T. E., Emran, A. M., and Kabalka, G. W., 1-[$^{11}$C]Butanol: synthesis and development as a radiopharmaceutical for blood flow measurements, *Int. J. Appl. Radiat. Isot.*, 36, pp. 412-413, 1985; Raiche, M. E., Eichling, J. O., Straatman, M. G., Welch, M. J., Larson, K. B., Ter-Pogossian, M. M., Blood-brain barrier permeability of $^{11}$C-labeled alcohols and $^{15}$O-labeled water, *Am. J. Physiol.*, Vol. 230, No. 2, 1976) and $^{14}$C labeled butanol (Ginsberg, M. D., Busto, R., and Harik S. I., Regional blood-brain barrier permeability to water and cerebral blood flow during status epilepticus: insensitivity to norepinephrine depletion, *Brain Research*, 337, pp. 59-71, 1985), show that butanol is freely permeable in the brain, due to its greater lipid solubility. Thus, the technique of using butanol for obtaining blood flow information has been clearly validated using $^{11}$C and $^{14}$C labeled butanol.

Notwithstanding the above, a very short-lived tracer is required for routine, sequential clinical positron emission tomographic studies. The long half-life of $^{11}$C and $^{14}$C (20 minutes) is inconvenient in common medical imaging procedures that use several sequential measurements of flow and measurements involving other radiopharmaceuticals. However, the short two minute half-life of $^{15}$O allows for repeat studies at ten minute intervals and also results in a low radiation dose to the patient. Therefore, it is now recognized that several sequential studies of one subject can be performed with improved accuracy if $^{15}$O-butanol is utilized as the tracer material.

Nevertheless, a problem that has slowed to some degree the use of butanol or any other alcohol labeled with $^{15}$O is that the processes available for the synthetic incorporation of $^{15}$O have not been sufficiently rapid or efficient. Along these lines, the two minute half-life of $^{15}$O has inhibited the overall production and use of $^{15}$O labeled alcohols as a tracer for positron emission tomography.

An additional restraint is that the tracer, once synthesized must be amenable to rapid purification. Along this line, the synthesized $^{15}$O-labeled butanol cannot be used for human subjects if it is not pure. $^{15}$O-labeled butanol is useless for quantitative studies if it contains the labeled by-product, $^{15}$O-labeled water. However, the two minute half-life of $^{15}$O limits the time available for purification. A very rapid but reliable purification process is necessary in order to produce useful quantities of good quality product.

In an attempt to overcome the above-noted difficulties, and to produce $^{15}$O butanol in an amount and quality sufficient for positron emission tomography use, the applicant previously described (Berridge, M. S., Franceschini, M. P., Tewson, T. J., and Gould, K. L., Preparation of oxygen-15 butanol for positron tomography, *J. Nucl. Med.* 27, pp. 834-839, 1986) a labeling procedure based on the work of Kabalka (Kabalka, G. W., Incorporation of stable and radioactive isotopes via organoborane chemistry. *Accts. Chem. Res.* 17, pp. 215-221, 1984; Kabalka, G. W. Lambrecht, R. M., Sajjad, M., Fowler, J. S., Wolf, A. P., Kunda, S. A., Mc- Collum, G. W., and MacGregor, R., Synthesis of $^{15}O$ labeled butanol via organoborane chemistry, 5th International Symposium on Radiopharmaceutical Chemistry, Tokyo, Japan, IV-P-24:265, 1985) with a tri-n-butylborane. Although the process described by Kabalka, et al. did not achieve a sufficiently high yield or purity in general use to allow for clinical applications, the basic reaction disclosed by Kabalka, et al. was utilized in applicant's process.

More particularly, in applicant's previous study, butanol was labeled with $^{15}O$ using the reaction of tri-n-butyl borane with oxygen gas in a glass vessel followed by C-18 cartridge purification. The preparation of $^{15}O$-butanol was performed using Kabalka's published reaction:

Furthermore, the $^{14}N(d,n)^{15}O$ reaction on nitrogen gas containing 1-2% oxygen was used in applicant's previous process for the production of $^{15}O$-labeled oxygen. The $^{15}O$ labeled oxygen was then reacted with tri-n-butyl borane by bubbling the $O_2$ through the tri-n-butylborane in a glass reaction vessel to produce a boron-complex, which was subsequently hydrolyzed by the addition of water. The solution was then purified through C-18 cartridge purification. A 50% conversion of $^{15}O$ to butanol was achieved through the use of this process with the remaining 50% comprised of labeled water. Pure butanol was recovered in about 10% radiochemical yield or 40% chemical yield with a synthesis time of four minutes.

However, while applicant's previous process was effective in producing $^{15}O$-labeled butanol, the production of butanol (i.e. 50 mCi) was too low for reliable clinical use. In addition, the production time for synthesis and purification, i.e. four minutes, was only marginal at best for positron emission tomography.

Subsequently to applicant's process, Ido and associates reported (Murakami, M., Hagami, E., Sasaki, H., Kondo, Y., Mizusawa, S., Nakamichi, H., Iida, H., Miura, S., Kanno, I., Vemura, K., and Ido, T., Radiosynthesis of $^{15}O$ labeled butanol for clinical use. *6th International Symposium Radiopharm. Chem.* 81, 1986) the use of a Sep-Pak C-18 cartridge (Waters Chromatography Div., Millipore Corp., Milford, Mass.) for both reagent support and purification with similar results. The Ido, et al. procedure was substantially similar to applicant's previous procedure except that [$^{15}O$] oxygen was trapped on the surface of the packed agent (an 18 carbon silane) in the micro column of a Sep-Pak C-18 cartridge, and a lower percentage of oxygen was present in the target gas (i.e. 0.5% $O_2$ in $N_2$). Specifically, the [$^{15}O]O_2$ was sent by helium gas flow to a Sep-Pak C-18 silane or silica cartridge which contained solvent-free tributyl borane (1 mmole). After the trapping of [$^{15}O]O_2$ (0.2 mmol), another Sep-Pak C-18 (C-18 carbone silane) cartridge was connected to the outlet. The 1.5 ml of water was passed through the two columns to hydrolyze the tributyl borane-$O_2$ complex. At this step, the radioactive impurity was eluted, and the unreacted tributylborane was retained in the cartridges. Subsequently, a strong amine exchange resin column ($OH^-$ type, 0.2 ml) was connected under the two Sep-Pak cartridges, and $^{15}O$-butanol was eluted by the addition of water to the three columns. At this step, the non-radioactive impurity was absorbed to the resin column. The eluate containing the $^{15}O$ butanol was then collected for clinical use. However, while Ido, et al. reported higher yields and purities, their results were difficult to reproduce. In addition, the product purity and/or yield of the Ido, et al. process may be insufficient for clinical use.

Applicant's present invention is directed to a new and improved method for synthesizing $^{15}O$-labeled butanol which overcomes the purity and yield restrictions produced by the prior art. In addition, in the investigation which produced the present invention, the applicant examined the effects of several parameters on the overall synthesis process for producing $^{15}O$-labeled butanol. The overall result is a new process and apparatus for producing $^{15}O$-labeled butanol which have sufficient product yield and purity for use in positron emission tomography.

SUMMARY OF THE INVENTION

In one aspect, the present invention is directed to a process for synthesizing $^{15}O$-labeled butanol with sufficient product yield and purity for autoradiographic and positron tomographic measurements of cerebral blood flow. The process is comprised of the initial steps of providing a target gas containing $^{15}O$-labeled oxygen (preferably 0.2%) in nitrogen gas and passing the target gas over an alumina (preferably hydrated gamma alumina) support containing a tri-n-butylborane reagent. The alumina support traps the labeled oxygen present in the target gas, thereby allowing the trapped gas to react (i.e. oxidize and label) the tri-n-butylborane reagent contained on the alumina support to produce an oxidized and/or labeled butyl-borane complex. Water is then added to the alumina support to hydrolyze the oxidized and/or labeled butyl-borane complex to produce a butyl-borane mixture containing labeled butanol which was released from the complex during the hydrolysis reaction. The hydrolyzed butyl-borane mixture containing the labeled butanol is subsequently washed or passed to a reverse phase support (preferably C-18 bonded phase silica) wherein the labeled butanol is collected. The reverse phase support containing the collected butanol is washed with water to remove the impurities produced by the oxidation and hydrolysis reaction indicated above in order to purify the labeled butanol product. The purified labeled butanol is then eluted from the reverse phase support by the use of a saline solution containing 10% ethanol. The eluted purified labeled butanol may then be immediately utilized for positron emission tomography.

In an additional aspect, the present invention is directed to an apparatus for synthesizing $^{15}O$-labeled butanol with sufficient product yield and purity for use in positron emission tomography. The apparatus is comprised of a means for providing a target gas comprised of $^{15}O$-labeled oxygen. An alumina support containing a tri-n-butylborane reagent is also provided wherein the alumina support has the ability to trap the $^{15}O$-labeled oxygen present in the target gas thereby enhancing the oxidation and labeling of the borane reagent by the labeled oxygen. The apparatus also contains a means for passing the target gas over the alumina support thereby oxidizing the tri-n-butylborane reagent contained thereon to produce an oxidized and labeled butyl-borane complex. A means for adding water to said alumina support is also produced thereby hydrolyzing the oxidized and labeled butyl-borane complex to produce a butyl-borane mixture containing labeled butanol. In addition, the apparatus contains a reverse phase support comprised of material for collecting the labeled butanol, and means for passing the hydrolyzed butyl-borane mixture through the reverse phase support wherein the labeled butanol from the mixture is collected. Furthermore, the apparatus contains a means for washing the reverse phase support containing the collected labeled butanol with water to purify the label butanol. A means for eluting the purified labeled butanol from the reverse phase support and a means for storing the eluted purified labeled butanol is also provided.

BRIEF DESCRIPTION OF THE DRAWINGS

The following is a brief description of the drawings which are presented for the purpose of illustrating the invention and not for the purpose of limiting same.

FIGS. 4A, 4B, and 4C are graphs indicating the effect of reagent cartridge age (i.e. the time elapsed after loading the tributylborane on the alumina cartridge) on the parameters of maximum yield of injectable butanol expressed as millicuries at the end of synthesis per microampere of beam current for a saturation bombardment (FIG. 4A); activity trapped on the alumina cartridge at E.O.B. (FIG. 4B); and, the percent of labeled butanol in the final product based on trapped oxygen (FIG. 4C).

DETAILED DESCRIPTION OF THE INVENTION

The present invention is directed to a process and apparatus for synthetically producing $^{15}$O-labeled butanol for positron emission tomography. In this regard, a procedure has been developed for the routine rapid and sequential synthesis of oxygen-15 labeled butanol in the amounts and with the purity suitable for use in clinical positron tomography. This procedure can replace oxygen-15 labeled water which is more commonly used for routine application, as well as applicant's previous process and the process described by Ido, et al. for producing oxygen-15 labeled butanol.

The synthesis of the present invention also uses Kabalka's published reaction (Kabalka, G. W., Incorporation of stable and radioactive isotopes via organoborane chemistry. Accts. Chem. Res. 17, pp. 215-221, 1984; Kabalka, G. W., Lambrecht, R. M., Sajjad, M., Fowler, J. S., Wolf, A. P., Kunda, S. A., McCollum, G. W., and MacGregor, R., Synthesis of $^{15}$O labeled butanol via organoborane chemistry, 5th International Symposium on Radiopharmaceutical Chemistry, Tokyo, Japan, IV-P-24:265, 1985) utilized in applicant's previous process for the production of $^{15}$O labeled butanol:

The accepted mechanism for the reaction is that the oxygen inserts into the borane to produce a B-O-O-Bu linkage. This then rearranges to form two B-O-Bu functions which release butanol on hydrolysis.

The above indicated reaction is exothermic and very rapid. However, applicant has determined that when the reaction is performed by bubbling gas containing oxygen through the liquid reagent, i.e. applicant's previous process, the rate of gas flow is restricted by the physical ejection of the liquid from the vessel, and by the limited efficiency of the contact between the gas and the liquid. As a result, the method of the present invention incorporates the suggestion of Ido, et al. (Murakami, M., Hagami, E., Sasaki, H., et al., Radiosynthesis of $^{15}$O labeled butanol for clinical use. 6th International Symposium Radiopharm. Chem. 81, 1986) to us a solid support to allow higher flow rates.

More specifically, in the present invention, the reagent tri-n-butyl borane is absorbed onto a solid support to prevent its removal in the gas stream and to increase contact between the tri-n-butyl borane reagent and the $^{15}$O labeled oxygen. Of particular importance in the present invention is the use of alumina, (i.e. a highly porous, granular form of aluminum oxide), as opposed to a silane (Ido, et al.), silica, sand, glass wool, etc., as the support. As more particularly discussed below, applicant has discovered that if alumina and more particularly, if a specific type of alumina such as hydrated gamma alumina is utilized as the packed material in the micro column or cartridge, the production yield and purity of the $^{15}$O-butanol reaction is greatly increased, i.e. the chemical yield of labeled butanol is raised from 50% to 80-90%.

Along this line, applicant has found that if alumina, silane, silica, sand, glass wool, etc. is utilized as the support, only a limited amount of labeled butanol (i.e. 50%) is produced. This yield is greatly increased if alumina, and particularly a specific type of alumina, i.e.

hydrated gamma alumina is used. If alumina activated by drying at 200° C. under vacuum is utilized, it produces both a significantly poorer trapping (as much as 40% less) of oxygen and a lower chemical yield (i.e. conversion) of butanol than that of hydrated gamma alumina. Overly wet alumina is similarly unusable and inconsistent in yield. However, alumina containing a water content between 5% and 20% gives optimum performance, with no clear preference within that range. Commercial chromatographic alumina (gamma) which is not specially activated falls within the same range and is therefore usable without any additional preparation. Neutral alpha alumina with a water content adjusted over the same range performed in a similar fashion, but an additional 25% to 30% of the activity was consistently found in the labeled water waste. Similarly, acidic gamma alumina sent more activity to waste, and basic gamma alumina was more similar to commercial neutral alumina but trapped somewhat less activity. This is thought to be because the alumina, and particularly the hydrated gamma alumina, participates not only as an inert support, but also plays an important role (see below) in directing the hydrolysis step which produces butanol.

In the present invention, $^{15}$O-labeled oxygen is produced by the same $^{14}$N(d,n)$^{15}$O reaction previously utilized by the applicant with 8 MeV deutrons on nitrogen gas containing oxygen. However, the percentage of $^{15}$O-labeled oxygen in the target gas is limited to 0.2% oxygen. The reduction of the oxygen content of the target gas (from 2% to 0.2% in nitrogen) improvement over applicant's previous process. Although alumina directs the reaction toward butanol, this does not occur when more than 1% oxygen is used with a corresponding amount of borane reagent. The reduction of oxygen also allows for the borane quantity to be reduced, thereby reducing the boron and carrier butanol present in the product.

In this regard, the applicant has found that a minimum concentration of 0.2% oxygen in the target gas proved quite satisfactory giving excellent yields in the process of the invention while reducing the carrier butanol level. Although the yields utilizing 0.2% oxygen as the target gas were not substantially different (i.e. 90% butanol yields) from those obtained with 0.5% and 1% oxygen, in the interest of producing less carrier in the $^{15}$O synthesis, 0.2% was chosen as the optimal oxygen concentration of the operating target gas.

Furthermore, in the process of the present invention, the labeled oxygen is applied to a micro column or cartridge containing hydrated alumina as the packed material wherein the hydrated alumina support material had been previously treated with the reagent tri-n-butyl borane. Along this line, the applicant has found that the optimal volume of tributylborane to be utilized with the 0.2% oxygen in the target gas is 75 μL (a small excess over a stoichiometer ratio with carrier oxygen). Although additional tributylborane reagent causes additional activity to remain on the alumina, applicant has found that if a volume of tributylborane slightly above the stoichiometric ratio with carrier oxygen is utilized, the yield decreases. Below this amount, the yield drops rapidly due to a lack of sufficient reagent to react with the available oxygen. As a result, a 75 μL injection of tributylborane in the system and apparatus of the present invention was therefore considered to be the optimum.

As a result of the addition of the labeled oxygen to the hydrated gamma alumina support, the labeled oxygen is trapped and allowed to react with the tri-n-butyl borane to produce an oxidized (and/or labeled) butylborane complex. The reaction with $^{15}$O-labeled oxygen is instantaneous and quantitative as the target gas (i.e. the $^{15}$O-labeled oxygen) travels rapidly through the column.

Rapid washing with water completes the hydrolysis and washes the hydrolyzed and labeled butanol from the alumina support onto a separate reverse-phase (large organic groups bound to silica) material for purification. The amount of this material is chosen to give optimal purification performance. Two commercially available C-18 Sep-Pak (Waters Associates, Milford, Mass.) containing 18 carbon silica proved to be well suited for use in the present invention. Since a significant amount of labeled butanol was consistently retained on the alumina surface, applicant experimented with different wash solutions and found that although basic pH solutions removed a larger quantity of labeled butanol than pure water, the slight gain in yield was insufficient to offset the additional processing requirements involved. Use of solutions containing oxidants, acids, or organic solvents and temperature variations from 0° to 70° C. had no desirable effects on the results. Moreover, the applicant also discovered that the optimal removal of butanol from alumina in the apparatus and process of the invention occurs at a total wash volume of 2-2.5 mL. In addition, it was also found to be advantageous to allow several seconds during the initial wash to hydrolyze the intermediate and released butanol. The optimal wash scheme, therefore is a 1 mL wash which is loaded onto the alumina cartridges and allowed to stand several seconds, followed by a 3 mL water wash.

The function of the reverse phase material (i.e. the C-18 silica cartridges) is to hold the labeled butanol so it can be washed free of water. Subsequent washing with water removes the unreacted borane containing impurities and the labeled water. Applicants have found that two C-18 cartridges were necessary to avoid premature removal of the butanol while washing it. The labeled butanol was retained on the double cartridges while labeled water was reduced to less than 0.4%, and often to zero after two to three washes with 0.5 mL portions of water.

The labeled butanol is then collected by eluting the reverse phase material, i.e. the C-18 cartridges, with sterile saline containing 10% ethanol. The product contains minimal levels of boric acid and carrier butanol and is sterile and pyrogen-free. The yield is 6 mCi per micro-ampere of saturated bombardment measured at the end of synthesis.

As a result of the use of an alumina support and/or target gas containing low oxygen content, as well as rapid purification techniques, up to 250 mCi of injectable $^{15}$O-labeled butanol can be produced in the present invention at ten minute intervals. This amount, i.e. a maximum production yield of 250 mCi, is comfortably in excess of the amounts required for chemical use. In addition, the quantities of the non-radioactive impurities present in the product carrier, are well below any physiological active dose.

The following example more particularly describes the specific embodiments of the present invention, as well as indicates the overall parameters and characteristics that were evaluated in order to produce the invention.

Materials and Methods

Tri-n-butylborane was obtained as the neat liquid from Aldrich Chemical or Alfa Products (Morton Thiokol) and stored under dry argon. Silica, alumina, and C-18 Sep-Paks were obtained from Waters Associates and prepared for reagent loading by flushing with dry argon. Chromatographic silica and gamma alumina were obtained from Universal Scientific and alpha alumina from Aldrich. Analysis of the product was performed by gas chromatography (GC) and liquid chromatography (HPLC). A Hewlett-Packard 5890 gas chromatograph with an Alltech RSL-150 (Polydimethylsiloxane, non-polar) capillary column was used with flame ionization detection. Conditions: temp. 70° C., He flow 5 mL/min. Retention times: water and EtOH, 0.69 min.; sec-butanol, 0.97 min; n-butanol, 1.3 min. A Spectra-physics 4270/8700 HPLC was used with an Alltech Econosil C-18 analytical column eluted with 15% acetonitrile in 0.01M ammonium acetate, at 2 mL/min. A Knauer refractive index detector and Beckman 170 radioactivity detector were used. Retention times of radioactive products were: water, 1.45 min.; sec-butanol, 4.4. min.; and n-butanol, 5.7 min.

Preparation of reagent

The optimum reagent support was chromatographic (gamma) alumina. Commercial cartridges were used for convenience, but chromatrograph alumina packed in glass or polypropylene micro columns or cartridges was equally useful. The cartridge was flushed with dry argon, and loaded under an argon atmosphere in a dry box by injecting 75 $\mu$L (0.3 mmol) of the liquid reagent (i.e. tri-butylborane) on the surface of the support. The cartridge was then sealed on each end with standard sleeve-septum stoppers (Thomas Sci.). The prepared reagent cartridges were stored in the dry box.

In addition, the applicant has also found that previously used cartridges have been successfully reused. They are recycled by washing with ethanol and acetonitrile, and then removing solvent with suction. They are then dried in vacuum (3 mm Hg, 80° C.) overnight and used as described above.

Synthesis of O-15 Butanol $^{15}$O-labeled oxygen was produced by the N(d,n)$^{15}$O reaction with 8 MeV deutrons on nitrogen gas containing 0.2% oxygen. The target was water-cooled aluminum, 161 mm long with a volume of 0.25 liters. It was pressurized to 6 atm and holds about 0.15 mmol of oxygen. The target window is two 0.025 mm havar foils with helium cooling.

Figure 1:
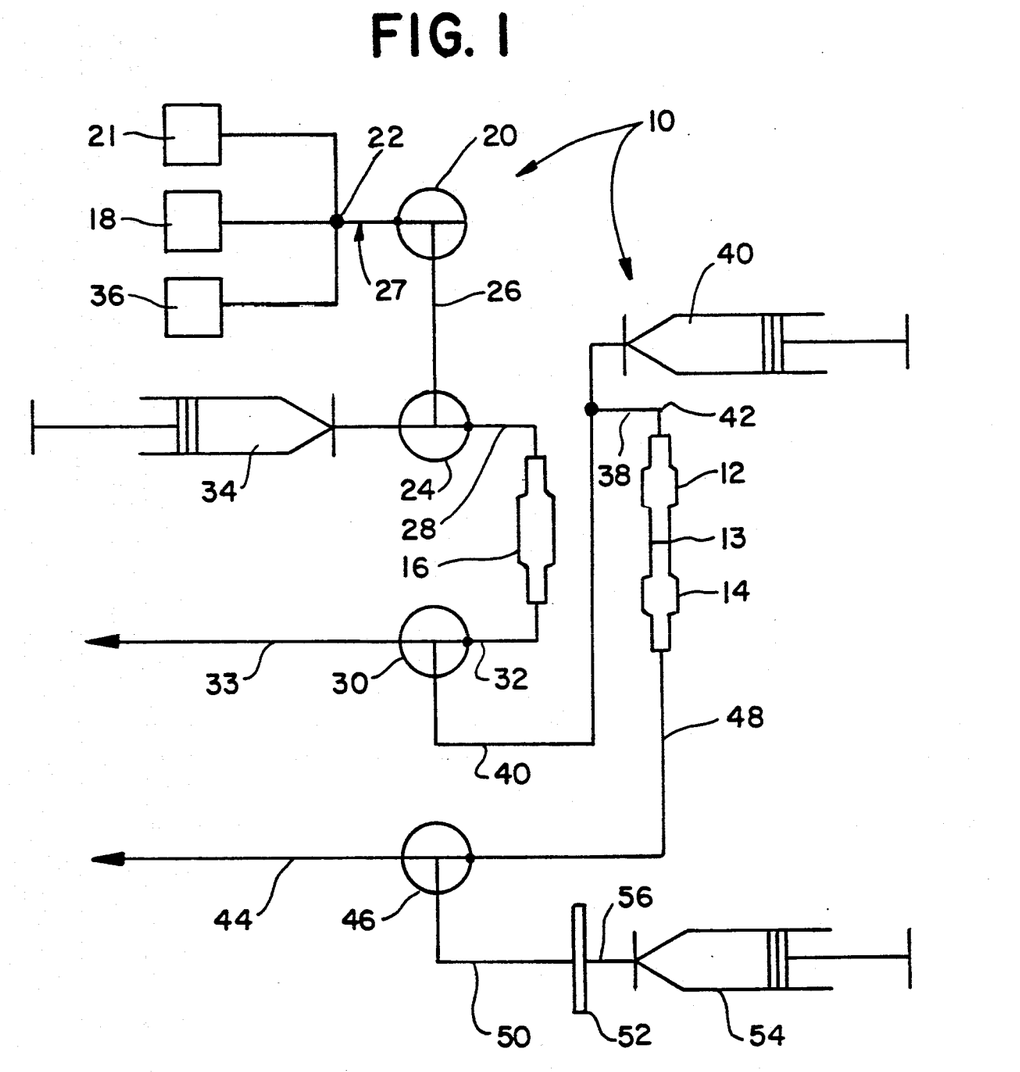
FIG. 1 is a diagram illustrating the $^{15}$O-butanol synthesis apparatus of the present invention.

The synthesis of $^{15}$O-labeled butanol was produced according to the butanol synthesis apparatus 10 shown in FIG. 1 by the following process. In this regard, two reverse phase cartridges 12 and 14, such as the reverse phase cartridges produced by Waters Associates C-18 Sep-paks #51910, were prepared by washing with ethanol according to manufacturer's instructions, joined with a short glass tube 13 and placed in the system 10, which was previously purged with helium. The helium had been added to the system 10 from helium source 18 by means of valve 22. A reagent cartridge or micro column 16 packed with either chromatographic silica, gamma alumina, alpha alumina, 18 carbon silane (C-18), sand, or glass wool and loaded with the tri-n-butylborane as indicated above was installed into system 10 within one minute before the end of bombardment (i.e. the production of the $^{15}$O-labeled oxygen as indicated above), with care taken to minimize exposure to air. The helium flow, i.e. from helium source 18, at 40 ml/min. was terminated by valve 22 at the end of bombardment.

Target gas (0.2% $O_2$ in $N_2$) produced by the $^{14}$N(d,n)$^{15}$O reaction with 8 MeV deutrons and stored in target 21 was emptied via valves 22, 20, and 24 and connective pipes 27, 26, and 28 into reagent cartridge 16 in 30 seconds at 3 L/minute using an additional pulse of unradiated target gas supplied from gas source 36 to the system by valves 22, 20, and 26 and interconnective piping 27, 26, and 28 to flush the $^{15}$O-labeled oxygen into the reagent cartridge 16. The $^{15}$O-labeled oxygen gas (i.e. the target gas) oxidized the tri-n-butylborane loaded onto the support material contained in the reagent cartridge 16 according to the formula set forth above. The waste gas was removed from the reagent column 16 via valve 30 and interconnective piping 32 to gas waste line 33. After 30 seconds, deionized water (1 mL) was injected by injector 34 into the reagent column 16 via valve 24 and piping 28, in order to hydrolyze the oxidized (and/or labeled) borane. This water was allowed to stand briefly while a second, 3 mL, water wash was prepared and inserted into injector 34. After 3 seconds, the second water wash was injected by injector 34 into the reagent cartridge 16 via valve 24 and piping 28. The second water wash was followed by the addition of 5 mL of air inserted into the system 10 from gas source 36 by the same procedure indicated above. These washes caused the butanol complex (i.e. the hydrolyzed labeled borane mixture) to move from the reagent cartridge 16 to the reverse phase cartridges 12 and 14 by means of valves 30 and 38 and interconnective piping 32, 40, and 42. The reverse phase cartridges collected the majority of the labeled butanol while the waste water containing boron-containing impurities and/or labeled water was emitted from the system 10 by liquid waste line 44 via piping 48 and valve 46. The waste gas was once again emitted from the system 10 to waste gas line 33 by valve 30 and piping 32.

The reverse phase material and the collected labeled butanol present in reverse phase columns 12 and 14 were then washed with three 0.5 ml portions of water which were not passed through the reagent cartridge 16. This was accomplished by adding the water to the reverse phase columns 12 and 14 by injecting the water into the system via injection 40, valve 38, and piping 42. 5 ml of 10% ethanol in sterile saline was then added to the reverse phase columns 12 and 14 by injector 40, and valve 38 and piping 42. The ethanol saline solution eluted the $^{15}$O-labeled butanol from the reverse phase columns 12 and 14. The eluted solution flowed through interconnective piping 48, valve 46, and piping 50 through a sterilizing filter 52 into a sterile syringe 54 by means of piping 56. The product was obtained at 2.5 minutes after the end of bombardment.

Nearly every variable in the above indicated procedure was altered during the investigation which produced the present invention and its effect on the yield and purity of the final product was determined. In this regard, the target gas flow, gas composition, amount of reagent, volume of wash water, wash method, type of solid reagent support, number of purification cartridges, and other parameters were all altered. In each case, the relevant changes can be considered to have been made singly or in combination with the above optimum procedure.

In addition, although the synthesis process was discussed above was originally performed, and most of the data obtained, with a manual system in which additions were made by syringes (i.e. injectors 34 and 40) through the two addition lines (FIG. 1), it would be a simple matter for one skilled in the art to automate the system as shown. A regulated gas supply may be used to drive water and the 10% ETOH/saline solution through the apparatus, as well as provide the necessary bursts of air. Solenoid valves may also be used to dispense air and fluids and direct their flow through the apparatus. Air and fluid volumes can be measured by timing the period that the dispensing valve is open. The exact timing may be determined empirically, depending upon gas pressure, and tubing lengths and diameters, etc. Aside from the obvious advantages of automation, this approach also speeds the set-up between clinical studies by eliminating the need to measure the fluid injections.

RESULTS

Table I below summarizes the results obtained using the reagent support system and washing procedure described above. This procedure has been used successfully in a routine clinical setting involving studies with repeated butanol injections. A bombardment of 15 microamps of 8 MeV deuterons for 10 minutes typically produced about 400 mCi of $^{15}O$ labeled oxygen at end of bombardment. From this amount, 100 mCi of patient-ready labeled butanol was prepared at 3 minutes after the end of bombardment. This product contains acceptably low levels of contaminating boric acid and carrier butanol, and has been found to be sterile and pyrogen-free. In applicant's system, the maximum routine beam current is 40 microamps, giving applicant a maximum yield of about 250 mCi of injectable butanol.

TABLE I

|  | Range | Best |
|---|---|---|
| Results |  |  |
| Trapped $O_2$ Activity | 250-300 | 330 |
| Chemical yield (%) | 80-90 | 94 |
| Radiochemical Yield (%) | 16-25 | 28 |
| % Activity Retained on Alumina | 15-18 | 7 |
| % Activity to Waste ($H_2O$ + BuOH) | 10-15 | 6 |
| % Activity Retained on C-18 | 10-12 | 8 |
| % Recovered Injectable BuOH | 55-65 | 84 |
| mCi Recovered Injectable BuOH | 50-70 | 84 |
| Analysis |  |  |
| % Water in Product (labeled) | 0-0.2 | 0 |
| % Sec-Butanol in Product | 4-6 | NA |
| Total Butanol in Product (mg) | 19-3 | 8.5 |
| Solid Residue (Boron compounds)(μg) | 40-200 | 0 |

Table I—Results obtained using the optimum procedure. For each parameter measured, the normal range is given as well as the best results obtained. In each case, the bombardment used was 15 microamperes for 10 minutes. Maximum practical beam current is 40 microamperes.

Figure 2:
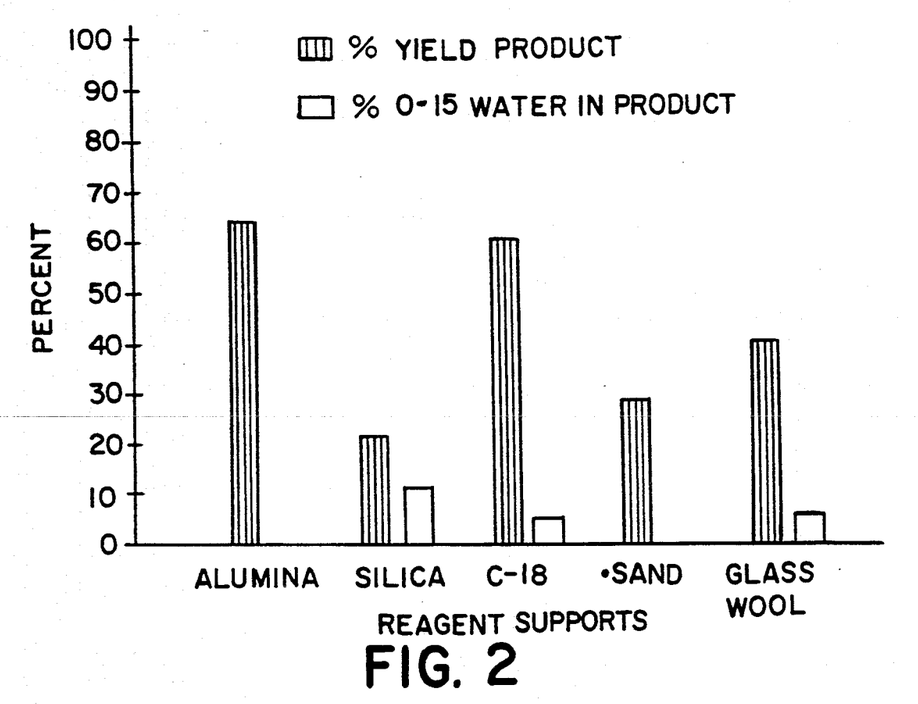
FIG. 2 is a graph showing the performance of various reagents as supports. For each support, the chemical yield (% yield product) of injectable butanol based on starting oxygen, and the percentage of water impurity (% $^{15}$O water) in that product is shown. In the case of sand, the purity was not determined, therefore, the chemical yield and purity is not shown in the FIGURE.

The use of a commercial alumina cartridge, or a similar cartridge prepared with chromatographic alumina, containing 0.075 mL of pure tri-n-butylborane provided the highest yield and purity of $^{15}O$ butanol. These prepared cartridges could be stored for several weeks under argon without loss of reactivity, however reactivity was lost within several days when the sealed cartridges were stored in room air. Silica, C-18, bonded silica, glass wool, and sand were not as effective as reagent supports (see FIG. 2). Alumina which had been activated by drying at 200° C. under vacuum gave both a significantly poorer trapping (as much as 40% less) of oxygen and a lower chemical yield of butanol. Overly wet alumina was similarly unusable and inconsistent in yield. Water content between 5% and 20% gives optimum performance, with no clear preference within that range. Commercial chromatographic alumina (gamma) which is not specially activated falls within the same range and is therefore usable without any additional preparation. Neutral alpha alumina with a water content adjusted over the same range performed in a similar fashion, but an additional 25% to 30% of the activity was consistently found in the labeled water waste. Similarly, acidic γ-alumina sent more activity to waste and basic γ-alumina was more similar to commercial neutral alumina but trapped somewhat less activity.

In order to reduce the amount of carrier butanol produced in the synthesis, applicant also studied the effects of the oxygen content of the target gas and the volume of tri-n-butylborane loaded on the cartridge. The target gas previously in routine use for $^{15}O$ syntheses was 1% oxygen in nitrogen. This was also satisfactory for production of butanol according to the present invention. A gas mixture with 2% oxygen was used for a short time, and the results were much less satisfactory. The maximum yield of butanol obtainable from 2% oxygen was 50% with the remainder found as labeled water. The oxygen content was then lowered below one percent in order to increase specific activity, and in the hope of further increasing the butanol yield. The minimum concentration tested was 0.2% oxygen, which proved quite satisfactory, giving excellent yields. The yields were, however, not substantially different from those obtained with 0.5% and 1% oxygen. In the interest of producing less carrier in all $^{15}O$ syntheses, 0.20% was chosen as the operating target gas. Excellent yields were also obtained using this gas to produce the other $^{15}O$ radiopharmaceuticals ($C^{15}O$, $H_2^{15}O$) with some modifications in the systems to adjust for the change in carrier quantity. For each concentration of oxygen in the target gas, the entire target yield was trapped on the reagent even at the highest gas flows obtainable on the system. This allowed the $^{15}O$ to be collected in as little as 20 seconds. Thus, as was reported previously by the applicant (Berridge, M. S., Franceschini, M. P., Tewson, T. J., and Gould, K. L., Preparation of oxygen-15 butanol for positron tomography, J. Nucl. Med. 27, pp. 834-839, 1986), the tributylborane reaction with oxygen is very rapid.

Figure 3:
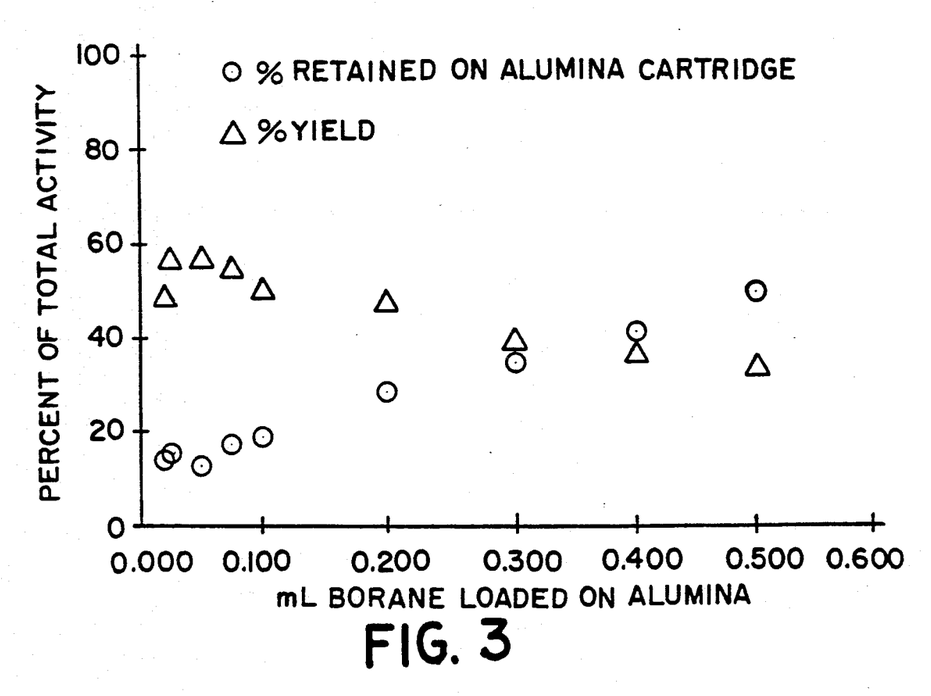
FIG. 3 is a graph demonstrating the effects of changing the volume of tri-n-butylborane based on the alumina cartridge (micro column) using the standard 0.2% oxygen in nitrogen as the target gas. Specifically, the graph illustrates the effect of borane on the chemical yield (triangles) of injectable butanol (based on starting oxygen), and on the amount of radioactivity retained on the alumina support (circles). The optimal wash procedure defined below was used in each case.

FIG. 3 shows the effects of changing the volume of tri-n-butylborane loaded on the alumina cartridge using the standard 0.2% oxygen in nitrogen as the target gas. An effect was observed on both the percentage yield and on the activity retained on the cartridge after washing. Clearly, as the reagent load is increased, additional activity simply remains bound on the cartridge. Above a volume of 75 μL (a small excess over a stoichiometric ratio with carrier oxygen), the yield decreases. Below this amount the yield drops rapidly due to a lack of sufficient reagent to react with the available oxygen. A 75 μL injection of tributylborane was therefore considered to be the optimum.

Figure 4A:
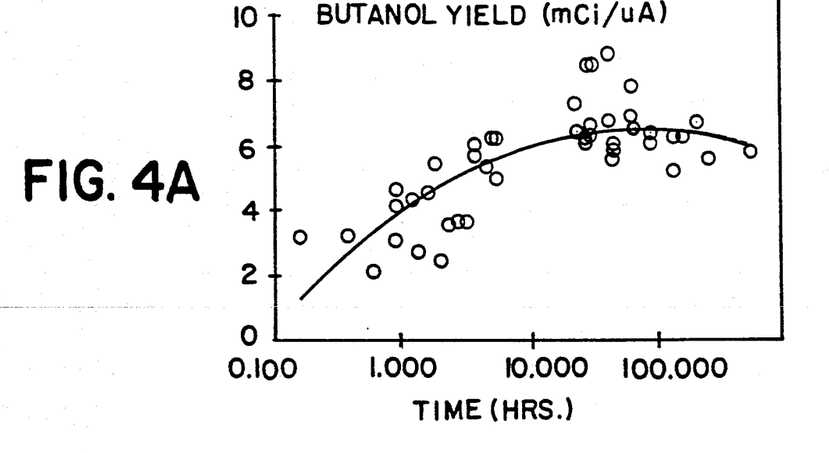
Figure 4B:
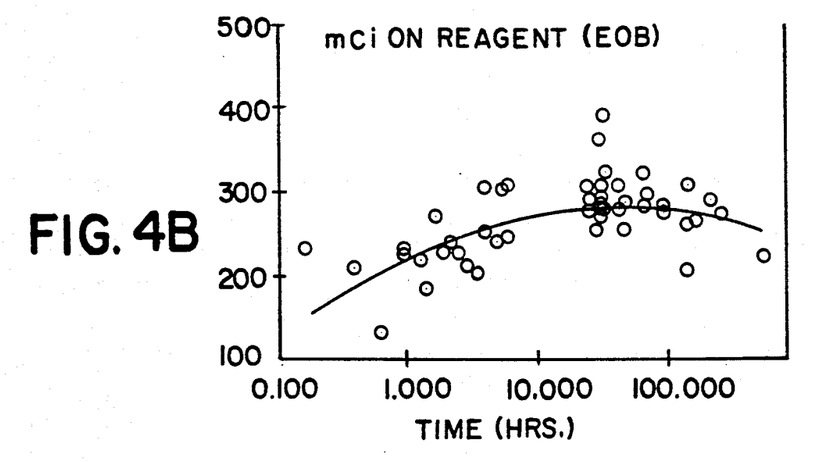
Figure 4C:
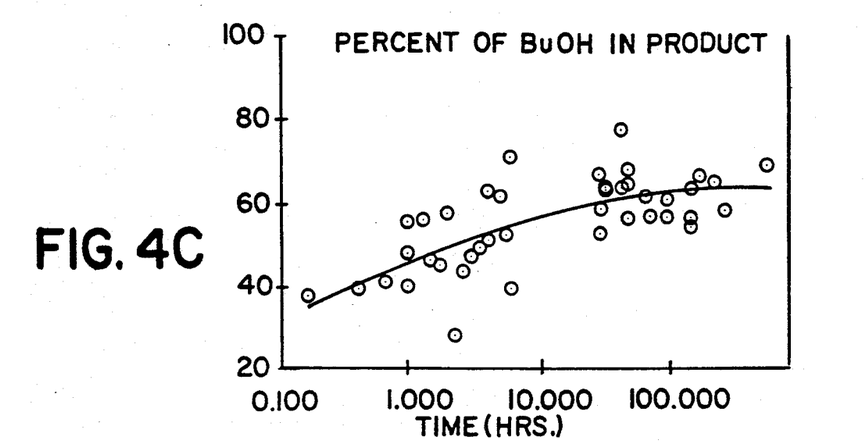

The time elapsed after loading the tributylborane on the alumina cartridge clearly and consistently affected several parameters. FIG. 4 shows that the three parameters affected are maximum yield, measured as mCi/μamp of injectable product, activity trapped on the alumina cartridge at EOB, and the percent of labeled butanol in the final patient-ready product. These are all maximized at 24–72 hours after loading the reagent onto the cartridge. Loaded cartridges are quite usable even 21 days after loading, provided they are stored under argon during that time. Freshly prepared cartridges (aged 15 min. up to 15 hours) do not show any differences in the product other than these yields, and they can therefore be used for clinical preparations provided that one allows for a perhaps significantly lower yield.

Since some activity containing a significant amount of labeled butanol was consistently retained on the reagent cartridge, chemical and physical methods for removing the additional activity were tried. Physical methods were unsuccessful. Reversing the alumina cartridge so that the tributylborane reagent was nearer to the cartridge exit during elution did not prove helpful in increasing yield or in reducing the activity retained on the Sep-Pak. Use of half-size alumina cartridges similarly provided no additional yield.

A variety of conditions for washing the activity (i.e. the labeled butanol) off of the reagent support were also investigated. Washing with $10^{-5}$N sodium hydroxide was perhaps marginally, but not significantly, better than plain water. Hydrogen peroxide at concentrations of 3% and 6% in water and in $10^{-5}$N NaOH, was also used. Solutions with a basic pH performed slightly better than the pure water reference. However, the slight gain in yield was insufficient to offset the additional processing requirements imposed by use of these reagents. Bicarbonate solutions were inadequate, producing a lower yield with poor product purity. Addition of 1–5% THF or ethanol and maintaining the reagent at temperatures from 0° to 70° C. during reaction had no desirable effects on the results.

Figure 5:
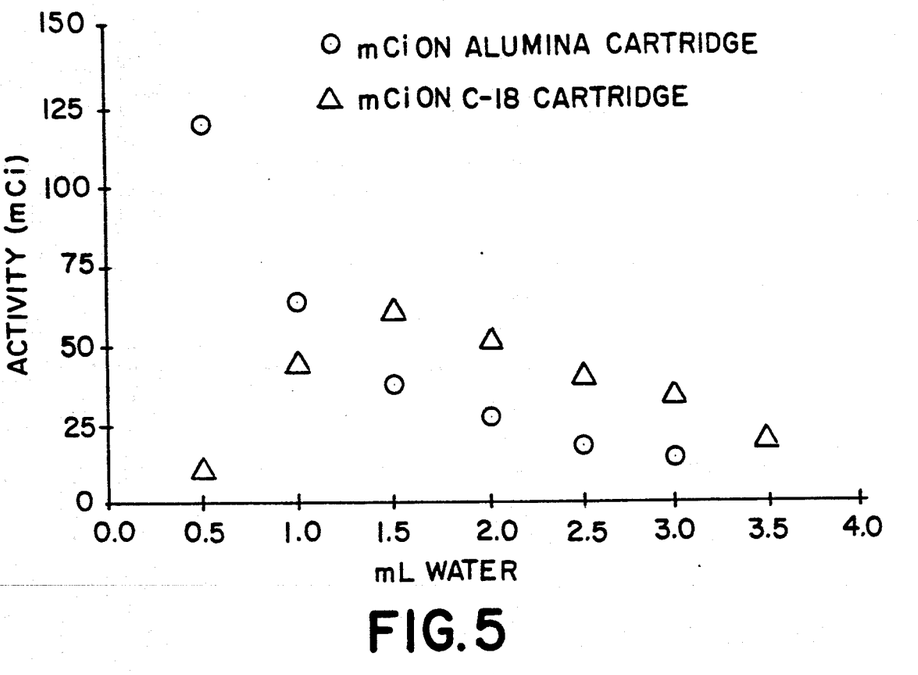
FIG. 5 is a graph showing the effectiveness of successive water washes in transferring activity from the reagent cartridge to the reverse phase cartridge. Specifically, FIG. 5 demonstrates the total radioactivity found on the alumina (circles) and C-18 (triangles) as a function of the volume of wash water (successive 0.5 mL washes) used to wash the alumina cartridge.

As a result of these experiments deionized water was chosen for washing the system. FIG. 5 shows the effectiveness of successive 0.5 mL washes in transferring activity from the reagent cartridge to the reverse-phase cartridge. Clearly, the maximum removal of radioactivity from the alumina occurs at the fourth or fifth 0.5 mL wash (total volume 2.0–2.5 mL). The remaining activity on the alumina cartridge appears tightly bound and is not reduced significantly by a further 3 mL of washing. It was also necessary to allow a short time (several seconds) during the wash to hydrolyze the oxidized tri-n-butylborane intermediate and release butanol. Therefore, the optimal wash scheme was determined to be a 1 mL wash which is loaded onto the cartridge and allowed to stand several seconds, while a second (3 mL) water wash is prepared and injected. A bolus of air (10 mL) after the second wash is sufficient to transfer the butanol to the reverse phase cartridges. HPLC analysis shows that the activity remaining on the reagent cartridge is high in labeled butanol (95%), but this last 10% of the activity was only removable with an organic solvent.

Figure 6:
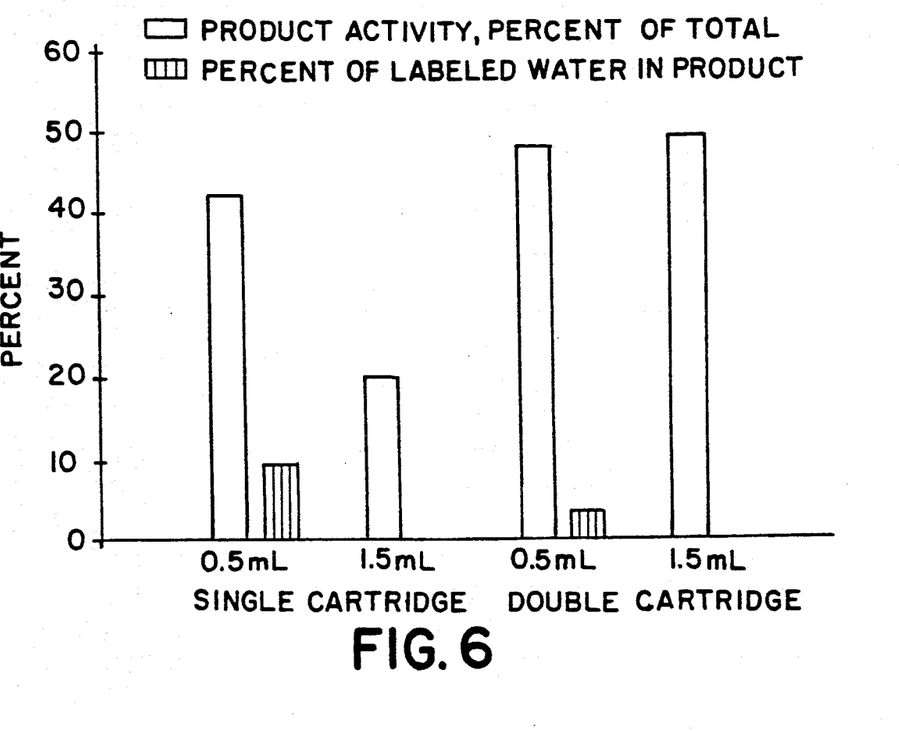
FIG. 6 is a graph demonstrating the advantage of using double C-18 cartridges in removing labeled water ($^{15}$O water) from the product. The total radioactivity in the product and the amount of labeled water in the product is shown as a function of the size of the C-18 cartridge wash bolus and of the number of C-18 cartridges used.
Figure 7:
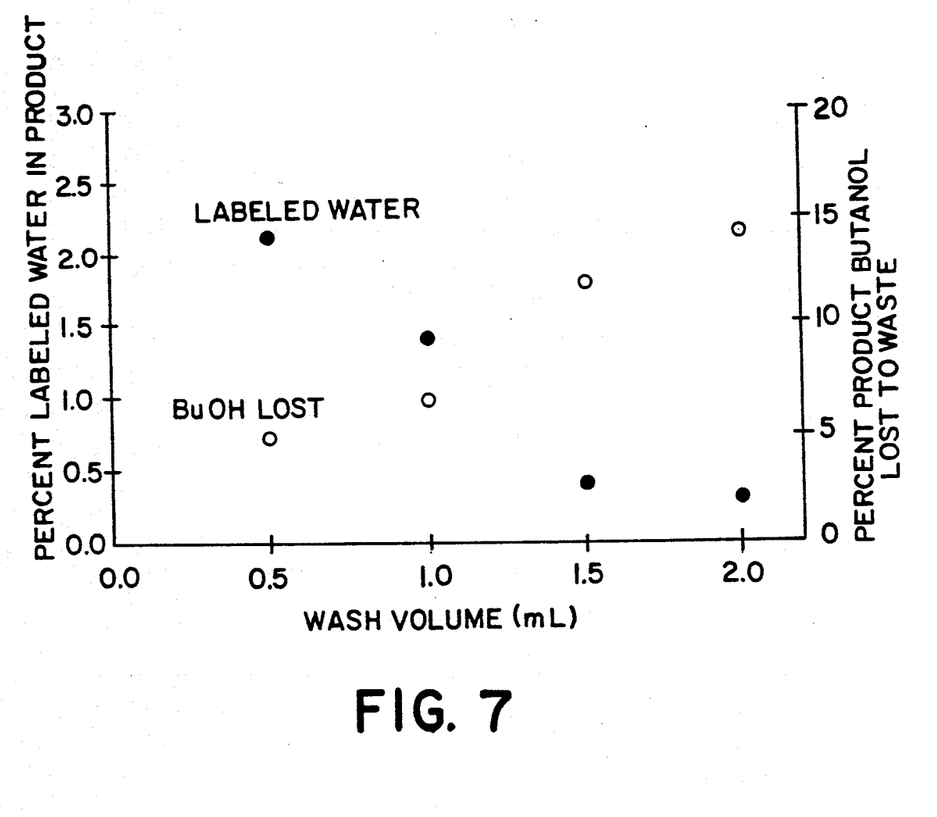
FIG. 7 graph showing the relationship of the percentage of labeled water in the product versus the percentage of labeled butanol washed to waste with successive 0.5 mL washes. Using a double C-18 cartridge, bolus washes of 0.5 mL were performed after using the optimum wash procedure to transfer activity from the alumina. The percentage of water in the produce (filled squares, left axis) and the amount of product lost to waste (circles, right axis) is shown.

The function of the C-18 cartridges is to hold the labeled butanol so it can be washed free of labeled water. FIG. 6 shows the advantage of using double C-18 cartridges in removing labeled water from the product. Washing the double cartridge with three 0.5 mL water washes reduced the labeled water content to less than 0.4% and often reduced it to zero. FIG. 7 shows the relationship of the percentage of labeled water in the product vs. the percentage labeled butanol washed to waste with successive 0.5 mL washes. The optimum combination of minimum loss of labeled butanol and an acceptable level of labeled water clearly occurs at the second 0.5 mL wash.

Discussion

Role of the Alumina Support

The use of alumina as a solid support for tri-n-butylborane is a major modification over applicant's previous method. This has ensured that over 90% of the $^{15}O_2$ produced reacts with the reagent, and has brought the chemical yield of butanol based on trapped oxygen to 80–90% as compared to the previous 50%. Consistent production of 50% labeled water was previously observed from use of both neat reagent and C-18 silica supported reagent (Ido, et al.). This has been dramatically reduced through the use of an alumina support, indicating that the alumina is acting not only as a support but is also taking part in the chemistry either as a reagent or catalyst.

Further evidence of involvement of the alumina in this reaction is that net butanol yield, oxygen trapping, and yield of injectable butanol all reached a maximum later than 15 hours after the application of tributylborane to the alumina (FIG. 4). Hydrated gamma alumina was unique in its ability to direct the reaction toward butanol production. The alpha form of alumina, as well as silica and reverse-phase bonded silica were significantly less effective in directing the reaction to produce butanol. Some water (5–20%) adsorbed on the alumina was necessary to increase yield and reduce water production, yet saturating the alumina with water reduced the yield significantly. Anhydrous gamma alumina performed no better than any other support.

The beneficial results noted above indicate that alumina is participating not merely as an inert support but is playing some role in directing the hydrolysis step which produces butanol. This role for the alumina as well as the particular results observed are consistent with the current knowledge of alumina as a catalyst. Although current theory of alumina catalyst is not exact, an accepted concept of interaction with the alumina surface has been devised in which a somewhat random distribution of ionic sites is present on the surface of gamma alumina. This distribution allows some clusters of anionic sites to form adjacent to a cluster of cationic sites, and this pair of sites is postulated to be responsible for the catalytic activity. Adsorption of water modifies the arrangement of ionic sites through addition of hydroxyl ions to the structure. Such a model explains the observations that only gamma alumina is active in directing the butanol synthesis. Alpha alumina, silica, and the other supports which were tested either do not have such sites or have them distributed in a more regular pattern which would preclude the formation of catalytically active clusters. The need for hydration is also explained since in high temperature dehydration of alumina, the number of surface hydroxyl groups may be reduced, thereby altering the distribution of the catalytic sites. Unfortunately, the applicant's present work does not allow this hypothesis to be tested and, in view of the uncertainty concerning the mechanism of this reaction, a detailed consideration of the role of the alumina is not justified. However, this alumina model does provide a basis for understanding the otherwise peculiar set of observations.

Close observation of the alumina after washing showed that the retained radioactivity was still located at the top of the cartridge, presumably where the tributylborane was first located, and had not migrated through the material with the 4 mL water wash. Reversing the cartridge so that it was washed in a last-in/first-out fashion also did not reduce the retained radioactivity. Therefore, the radioactivity which is not readily removed by water (as labeled butanol and water) must be found to the support in another, undetermined, chemical form. After hydrolysis of oxidized tributylborane the labeled oxygen may remain bound to boron which is bound or tightly associated with alumina. Another possibility is that some labeled oxygen binds to aluminum atoms or exchanges with oxygen in the alumina structure.

The observation that very little boron is found in even the crude product confirms the expected results that many boron compounds are not readily washed off of the alumina. A further observation in support of this point is that the only boron compound isolated from the system was boric acid, $B(OH)_3$. The $BuB(OH)_2$ which was observed in abundance during previous work (Berridge, M. S., Franceschini, M. P., Tewson, T. J., and Gould, K. L., Preparation of oxygen-15 butanol for positron tomography, J. Nucl. Med. 27, pp. 834–839, 1986) either was not produced using this method or was not removed from the alumina.

Reduction of the oxygen content of the target gas (from 2% to 0.2% in nitrogen) is another significantly improvement over the applicant's original method. Although the interaction of the alumina support is needed to direct the reaction toward butanol, this effect is not observed when a 2% oxygen mixture (1.5 mmol) is used with a corresponding amount of borane reagent. The effect was only observed upon dropping the oxygen content below 1%. This is possibly due to the physical limits imposed by the size of an alumina cartridge on the amount and distribution of the borane load that can be achieved. The change to 0.2% oxygen allowed reduction of tributylborane to 75 $\mu L$ without affecting trapping or yield, but effectively reducing the amount of boric acid and carrier butanol produced. The ratio of oxygen to tributylborane also appears to be a factor. Increasing the quantity of tributylborane (using 0.2% oxygen) gave the same excellent trapping of oxygen and net butanol yield, but less butanol was removable from the alumina by washing with water (FIG. 3), so that the practical yield of butanol was reduced.

Clinical Utility of the Method

There were several factors in the synthesis which had a significant effect on the product yield or purity. As discussed above, the choice of hydrated gamma alumina as the support, and the use of a low concentration of oxygen in the target gas were very important in achieving a high yield of butanol. Also important is the use of a rapid washing procedure to purify the product. This, combined with the ease of using a solid support, has allowed the synthesis time to as short as 2.25 minutes. Considering the half-life of two minutes, this could well be the most significant improvement offered by the new method. In applying this procedure to the production of $^{15}O$-butanol for clinical use, it is important to take advantage of each of these factors. In applicant's hands, the maximum production yield of 250 mCi is then comfortably in excess of the clinical requirement of 10–100 mCi per injected dose.

Another factor enhancing the clinical utility of the method is the simplicity of the apparatus and procedure. While the butanol synthesis is more complex than the synthesis of $^{15}O$-water, it remains possible to clean and reload the apparatus rapidly enough to produce sequential batches within the preferred ten minute delay between blood flow measurements. This is largely due to the fact that the reagent and purification cartridges and washing solutions can be prepared in advance. As noted in FIG. 4, it is not only possible, but preferred, to prepare reagent cartridges at least several hours before use. Although the applicant has not had any occasion to use cartridges older than 21 days, they remain useful up to that age. The evidence indicates that the reagent cartridge should have no built-in expiration date. Rather, the practical age limit seems to be determined by the tightness of the cartridges seals and they inertness of the atmosphere in which they are stored. Cartridges stored in room air completely lose their ability to make butanol after several days, but this could be improved by using a more air-tight cartridge and seal. For routine use, it is preferable to store the cartridges under argon and to prepare the necessary quantity once each week.

Analyses by radio-HPLC of the crude reaction product consistently showed three products. $^{15}O$ water eluted at 1.5 min. and was virtually eliminated by sufficient washing and by using two reverse phase cartridges. A product eluting at 4.4 minutes was identified by HPLC and GC as $^{15}O$-sec-butanol and comprised 4–6% of the total product activity. It originated from sec-butyls present in the tri-n-butylborane and was not separable from the n-butanol without HPLC. Since the utility of the radiopharmaceutical as a blood flow tracer is dependent primarily on its lipophilicity, the presence of sec-butanol as a minor impurity would not be expected to significantly alter measurements of blood flow made using n-butanol and was therefore considered to be acceptable. The major components is, of course, n-butanol. The usual composition of the product is therefore 95% n-butanol, 5% sec-butanol, with an occasion trace of labeled water.

The yield and the product composition are significantly affected by small changes in the procedure for washing the reagent and purification cartridges. The actual volume required for each wash will vary with the size of the cartridges, the amount of reagent, and the flow rate of the wash. The important point in washing the reagent cartridge is to use the minimum volume necessary to recover the removable radioactivity (FIG. 5). This must be balanced against elution of the desired butanol to waste (FIG. 5). A larger charge of reverse-phase material (FIG. 6) helps to retain the butanol during added washes of the alumina cartridge. In applicant's hands, two commercial reverse-phase cartridges were sufficient.

It was not possible to use the washes of the alumina for the double purpose of washing the C-18 cartridges. A portion of the radioactivity remaining on the alumina eluted slowly as labeled water. If the wash water for the C-18 cartridges was allowed to pass over the alumina, this water "bleed" would remain with the butanol and contribute a measurable amount of labeled water to the final product. When the C-18 cartridge assembly was washed individually, the last of the labeled water was removed. The results of washing these cartridges (FIG. 7) show that some labeled butanol is lost to waste with the water. There is, therefore, a compromise to be reached between the product yield and the amount of water impurity. A 1 mL wash gives little excess loss of butanol, but allows around one percent of the product to be labeled water. Increasing the wash to 1.5 mL doubles the loss of butanol to waste, but in most cases, lowers the water impurity to zero, with an upper limit of 0.2 percent. It is not clear what level of water impurity would be needed to adversely affect a blood flow measurement made using butanol. For the moment, applicant has chosen to sacrifice some yield in favor of near-absolute purity. Nearly forty percent of the butanol synthesized is therefore lost to the washes, leaving 50% of the activity at the end of synthesis as useful product.

The quantity of the non-radioactive impurities present in the product (butanol carrier and boric acid, Table I) is well below any quantity which has been observed to have any physiological effects. The toxic doses of butanol and of boric acid are in the range of grams to tens of grams, and normal serum contains 0.1–0.2 mg. of boron per deciliter.

In summary, through the process of the present invention, oxygen-15 labeled butanol can be produced from tri-n-butylborane in amounts exceeding that necessary for routine positron emission tomography use. A 10 minute, 8 MeV deuteron bombardment at 15 μamps can be expected to produce 100 mCi consistently. The maximum routinely producible quantity using the cyclotron is 250 mCi. The synthesis is sufficiently rapid and simple that sequential doses may be prepared at eight minute intervals. The actual synthesis and purification requires up to three minutes. The purity and toxicity of the product are well within prudent limits. This method represents a significant advance in simplicity, speed, and reliability over applicant's previously published approach, as well as that known in the prior art.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A process for synthesizing $^{15}$O-labeled butanol with sufficient product yield and purity for use in positron emission tomography comprising the steps of:
   a) providing a target gas comprised of $^{15}$O-labeled oxygen;
   b) passing the target gas over an alumina support containing a tri-n-butylborane reagent thereby trapping the $^{15}$O- labeled oxygen gas in the support, wherein said trapped $^{15}$O-labeled gas oxidizes and labels the borane reagent contained on the alumina support to produce an oxidized and labeled butyl-borane complex;
   c) adding water to the alumina support to hydrolyze the oxidized and labeled butyl-borane complex thereby releasing labeled butanol and producing a butyl-borane mixture containing same;
   d) passing the hydrolyzed butyl-borane mixture containing the labeled butanol over a reverse phase support to collect the labeled butanol;
   e) washing the reverse phase support containing the collected labeled butanol with water to remove the impurities produced by the oxidation and hydrolysis steps thereby purifying the labeled butanol; and,
   f) eluting the purified labeled butanol from the reverse phase support thereby collecting the purified labeled butanol.

2. The process of claim 1, wherein said target gas is comprised of from about 0.1% to about 1% oxygen in nitrogen.

3. The process of claim 1, wherein said target gas is comprised of 0.2% oxygen in nitrogen.

4. The process of claim 1, wherein said alumina support is gamma alumina.

5. The process of claim 1, wherein said alumina support is comprised of hydrated gamma alumina.

6. The process of claim 1, wherein said alumina support contains from about 5% to about 20% water.

7. The process of claim 1, wherein said reverse phase support is comprised of silica material bonded to large organic groups.

8. The process of claim 1, wherein said reverse phase support is comprised of a sufficient amount of silica material bonded to large organic groups to minimize the amount of labeled water associated with the labeled butanol while maximizing the amount of labeled butanol present.

9. The process of claim 1, wherein said reverse phase support is comprised of at least one reverse phase cartridge containing C-18 bonded phase silica.

10. The process of claim 1, wherein said reverse phase support is comprised of two C-18 bonded phase silica cartridges operably connected to one another.

11. The process of claim 1, wherein said purified labeled butanol was eluted from the reverse phase support with sterile saline containing 10% ethanol.

12. The process of claim 1, wherein said impurities include labeled water.

13. The process of claim 1, wherein said water is added to the alumina support to hydrolyze the oxidized butyl-borane complex and to wash the hydrolyzed mixture to the reverse phase support in two separate increments of water of 1 mL and 3 mL each.

14. The process of claim 1, wherein said alumina support contains a sufficient amount of tri-n-butylborane such that the tri-n-butylborane is in stoichiometric ratio with the carrier oxygen.

15. The process of claim 1, wherein said alumina support contains 0.075 mL of tri-n-butylborane.

16. The process of claim 1, wherein said target gas is passed over the alumina support containing the tri-n-butylborane reagent within 24 to 72 hours after loading said tri-n-butylborane reagent onto the alumina support.

17. The process of claim 1, wherein the chemical yield of labeled butanol based on trapped oxygen is about 80%.

18. A process for synthesizing oxygen-15 labeled butanol suitable for use in positron emission tomography comprising the steps of:
   a) producing a target gas comprised of $^{15}$O-labeled oxygen by the $^{14}$N(d,n)$^{15}$O reaction with 8 MeV deuterons on nitrogen gas containing 0.2% oxygen;
   b) preparing a reagent support cartridge by injecting 0.075 tri-n-butylborane onto the support surface of a reagent cartridge packed with hydrated gamma alumina;
   c) passing the target gas over the reagent support cartridge thereby oxidizing and labeling the borane compound to produce an oxidized tri-n-butylborane intermediate;
   d) adding deionized water into the gamma alumina support surface of the reagent cartridge to hydrolyze the oxidized tri-n-butylborane intermediate thereby releasing labeled butanol;

e) passing the hydrolyzed borane mixture containing the released labeled butanol over a reverse phase support containing C-18 bonded phase silica to collect the labeled butanol f) washing the reverse phase silica material containing the collected labeled borane with deionized water to remove the labeled water and the boron-containing impurities thereby purifying the collected labeled butanol;

g) washing the reverse phase silica material containing the purified labeled butanol with sterile saline containing 10% ethanol in order to elute the labeled butanol from the reverse phase silica material; and, h) collecting the eluted labeled butanol.

* * * * *